United States Patent
Cheng

(10) Patent No.: US 6,178,561 B1
(45) Date of Patent: Jan. 30, 2001

(54) SAFETY GOGGLES HAVING A LENS FRAME FORCE-FITTED IN A PRIMARY FRAME

(76) Inventor: Chen-San Cheng, P.O. Box 82-144, Taipei (TW)

(*) Notice: Under 35 U.S.C. 154(b), the term of this patent shall be extended for 0 days.

(21) Appl. No.: 09/409,231

(22) Filed: Sep. 30, 1999

(51) Int. Cl.⁷ .................................................... A61F 9/02
(52) U.S. Cl. .................................. 2/431; 2/8; 2/441; 2/13
(58) Field of Search ............................... 2/431, 434, 439, 2/440, 441, 442, 443, 453, 8, 10, 13

(56) References Cited

U.S. PATENT DOCUMENTS

| | | | |
|---|---|---|---|
| 2,998,610 | * | 9/1961 | Spero ......................................... 2/13 |
| 3,901,589 | * | 8/1975 | Bienenfeld ............................. 2/13 X |
| 5,533,208 | * | 7/1996 | Tonoyan et al. ............................ 2/10 |

\* cited by examiner

*Primary Examiner*—Peter Nerbun
(74) *Attorney, Agent, or Firm*—A & J

(57) ABSTRACT

Safety goggles include a primary frame having a top provided with two raised seats and an upwardly extending tongue between the two raised seats, each of the seats having a first pin extending outwardly longitudinally from an end thereof and a second pin extending outwardly longitudinally from another end thereof, a lens frame having a top provided with two cavities aligned with the two raised seats, each of the cavities being formed with a groove and an opening configured to receive the first pin and the second pin respectively, a recess being formed between the two cavities and aligned with the tongue, the recess having an inclined surface at an outer side thereof and a chamfer at an inner side thereof, the chamfer being located close to the opening, whereby the goggles can be rapidly manufactured and assembled.

3 Claims, 5 Drawing Sheets

SAFETY GOGGLES HAVING A LENS FRAME FORCE-FITTED IN A PRIMARY FRAME

BACKGROUND OF THE INVENTION

1. Field of the Invention

This invention is related to an improvement in the structure of safety goggles and in particular to one which can be easily manufactured and assembled.

2. Description of the Prior Art

The conventional safety goggles generally includes a primary frame 10 and a lens frame 20. The primary frame 10 is provided at the top of its front side with two raised seats 101 each having an axial through hole 1011 and an upwardly extending tongue 102 located between the two raised seats 101. The lens frame 20 is provided at the top with two cavities 201 aligned with the two raised seats 101 and a recess 202 located between the two cavities 201 and aligned with the tongue 102. The recess 202 is formed with an inclined surface 203 at the front side. The upper portion of the lens frame 20 has an axial through hole 204 aligned with the axial through hole 1011 of the primary frame 10. When in assembly, the raised seats 101 are first fitted into the cavities 201 with the tongue 102 disposed in the recess 202 and then two pins 30 are inserted from two opposite sides into the holes 204 of the lens frame 20 and the holes 1011 of the primary frame 10 see FIGS. 1, 2 and 3). Accordingly, the lens frame 20 is pivotally connected with the raised seats 101 of the primary frame 10, so that when the lens frame 20 is turned down on the primary frame 10, the rim 103 of the primary frame 10 will be just covered by the outer rim 205 of the lens frame 10 thereby making it suitable for protecting one's eyes in gas welding or cutting operation. As shown in FIG. 4, the tongue 102 is made of plastic, so that when the lens frame 20 is turned upwards, the rear side of the recess 202 will be rotated to engage with the tongue 102 so as to keep the lens frame 20 in a fixed position.

However, it is necessary to force two pivot pins 30 into the lens frame 20 and the primary frame 10 in order to join them pivotally together thus requiring a lot of time and effort in the assembly. Furthermore, the goggles are easily damaged when the pivot pins 30 are forced into the lens frame 20 and the primary frame 10. In addition, once the pivot pins 30 are forced into the lens frame 20 and the primary frame 10, it is no longer possible to disengage the lens frame 20 from the primary frame 10 thereby increasing the difficulties in processing operations.

Therefore, it is an object of the present invention to provide an improvement in the structure of safety goggles which can obviate and mitigate the above-mentioned drawbacks.

SUMMARY OF THE INVENTION

This invention is related to an improvement in the structure of safety Goggles.

According to a preferred embodiment of the present invention, the safety goggles include a primary frame having a top provided with two raised seats and an upwardly extending tongue between the two raised seats, each of the seats having a first pin extending outwardly longitudinally from an end thereof and a second pin extending outwardly longitudinally from another end thereof, a lens frame having a top provided with two cavities aligned with the two raised seats, each of the cavities being formed with a groove and an opening configured to receive the first pin and the second pin respectively, a recess being formed between the two cavities and aligned with the tongue, the recess having an inclined surface at an outer side thereof and a chamfer at an inner side thereof, the chamfer being located close to the opening.

It is the primary object of the present invention to provide an improvement in the structure of safety goggles which can be rapidly assembled.

It is another object of the present invention to provide an improvement in the structure of safety goggles which can be easily manufactured.

It is still another object of the present invention to provide an improvement in the structure of safety goggles which is simple in construction.

It is still another object of the present invention to provide an improvement in the structure of safety goggles which is low in cost.

It is a further object of the present invention to provide an improvement in the structure of safety goggles which is fit for mass production.

The foregoing objects and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts. Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENT

Figure 1:
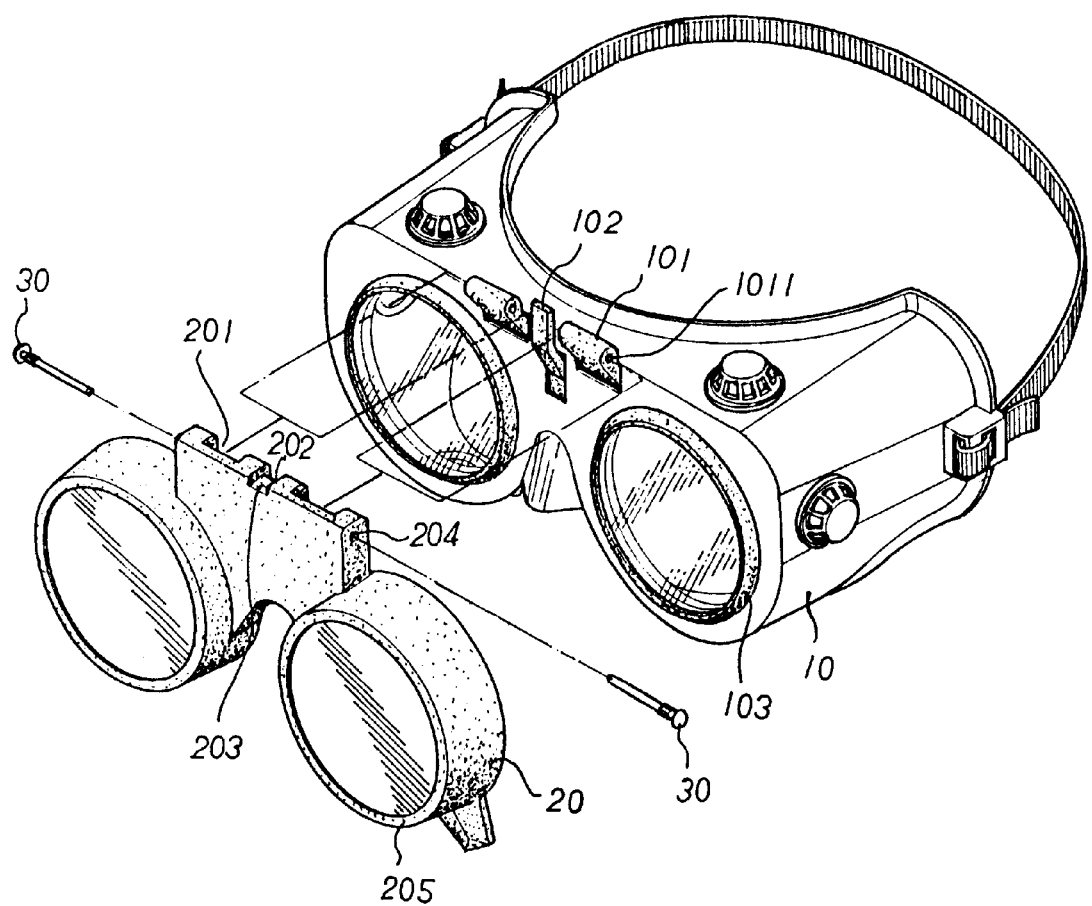
FIG. 1 is an exploded view of prior art safety goggles.
Figure 2:
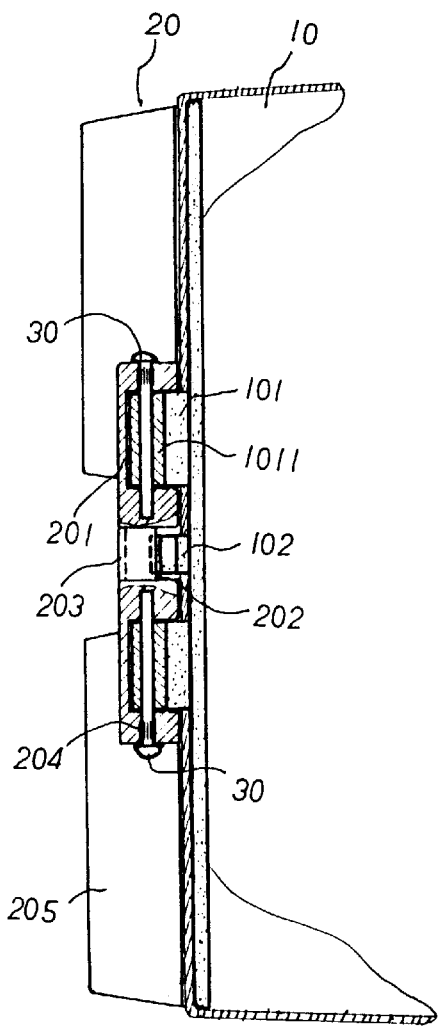
FIG. 2 is a sectional top view of the prior art safety goggles.
Figure 3:
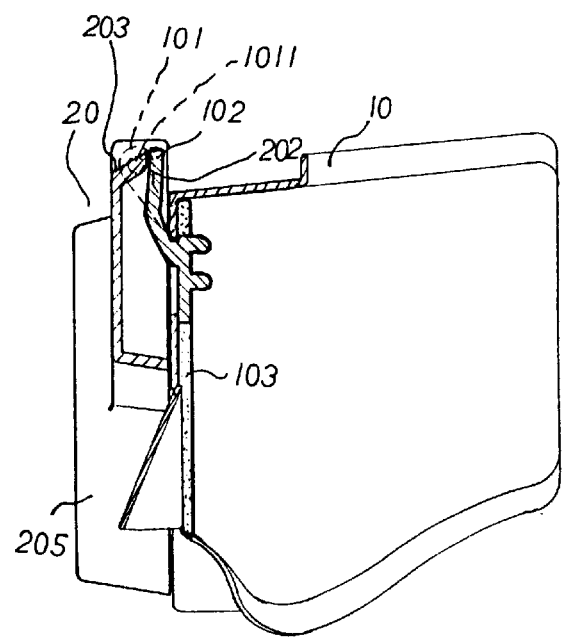
FIG. 3 is a sectional side view of the prior art safety goggles.
Figure 4:
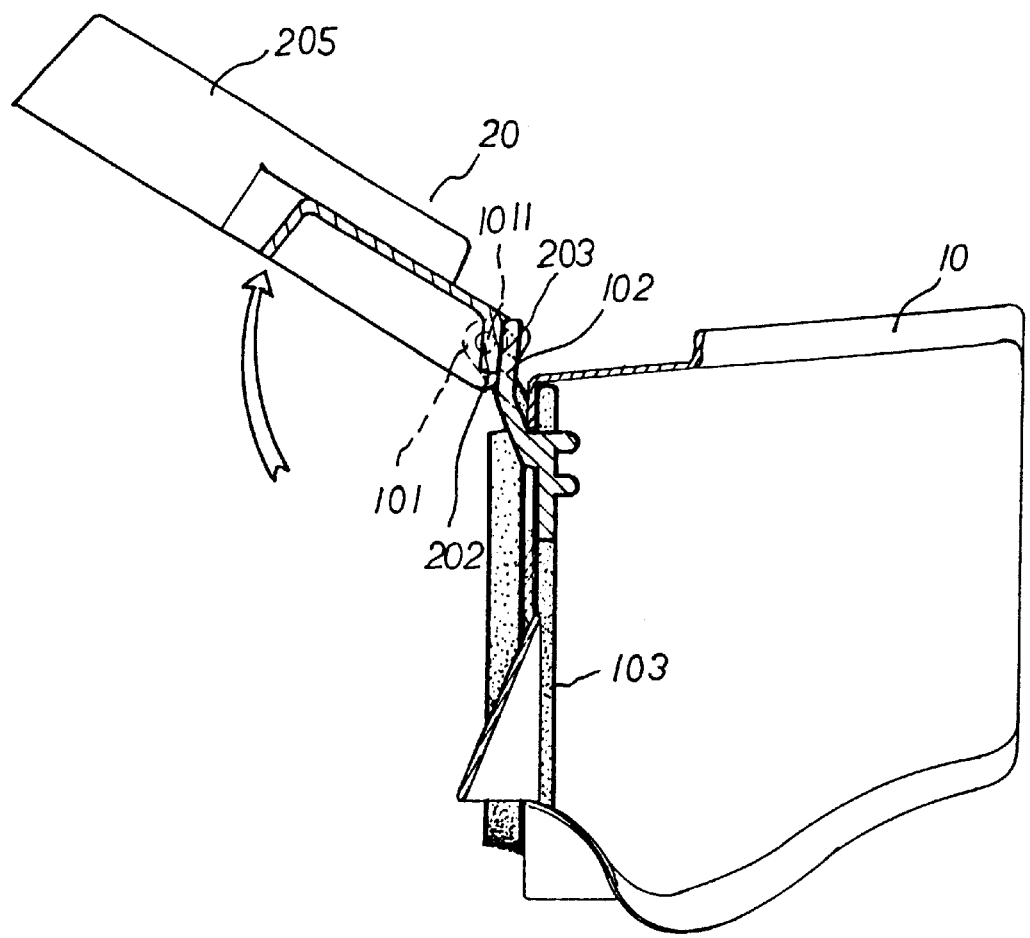
FIG. 4 illustrates the assembly of the prior art safety goggles.

For the purpose of promoting an understanding of the principles of the invention, reference will now be made to the embodiment illustrated in the drawings. Specific language will be used to describe same. It will, nevertheless, be understood that no limitation of the scope of the invention is thereby intended, such alterations and further modifications in the illustrated device, and such further applications of the principles of the invention as illustrated herein being contemplated as would normally occur to one skilled in the art to which the invention relates.

Figure 5:
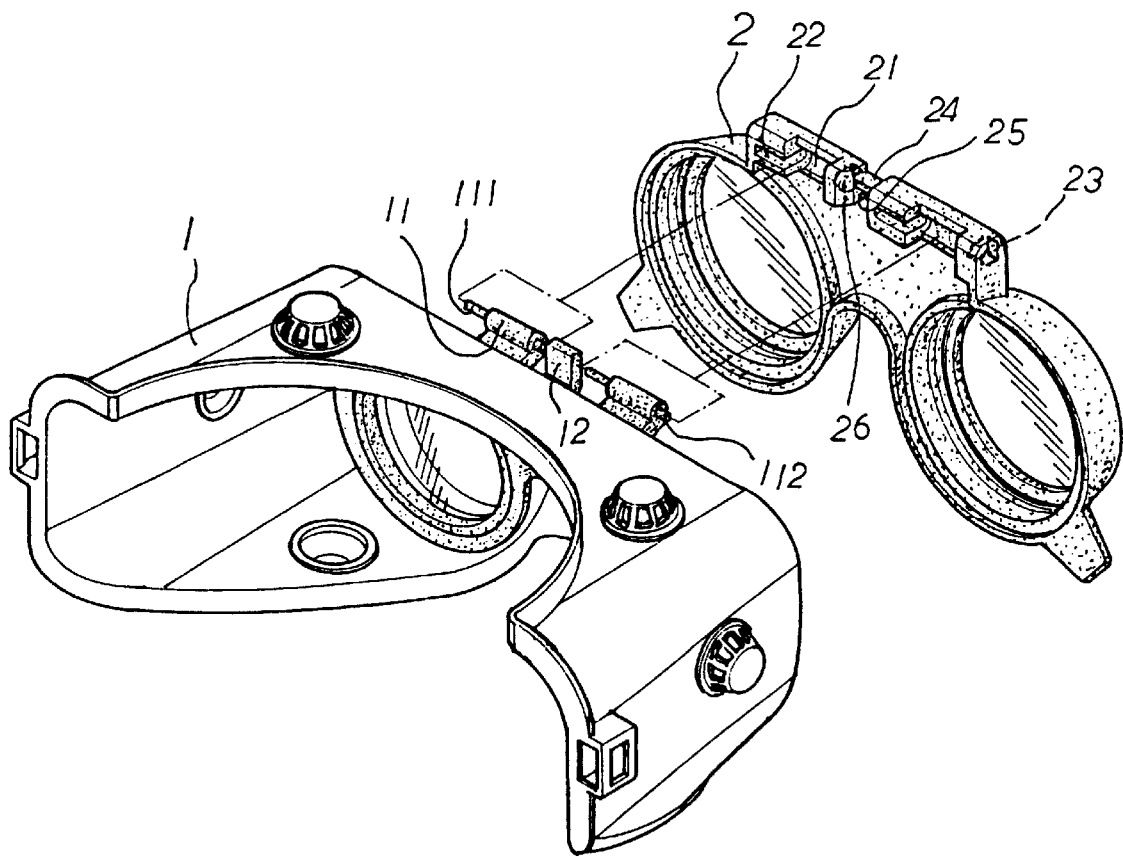
FIG. 5 is an exploded view of the safety goggles according to the present invention.

With reference to the drawings and in particular to FIG. 5 thereof, the goggles according to the present invention generally comprise a primary frame 1 and a lens frame 2.

The primary frame 1 is provided at the top of its front side with two raised seats 11 and an upwardly extending tongue 12 between the two raised seats 11. Each of the seats 12 has a long pin 111 extending outwardly longitudinally from an end thereof and a short pin 112 extending outwardly longitudinally from another end thereof.

Figure 6:
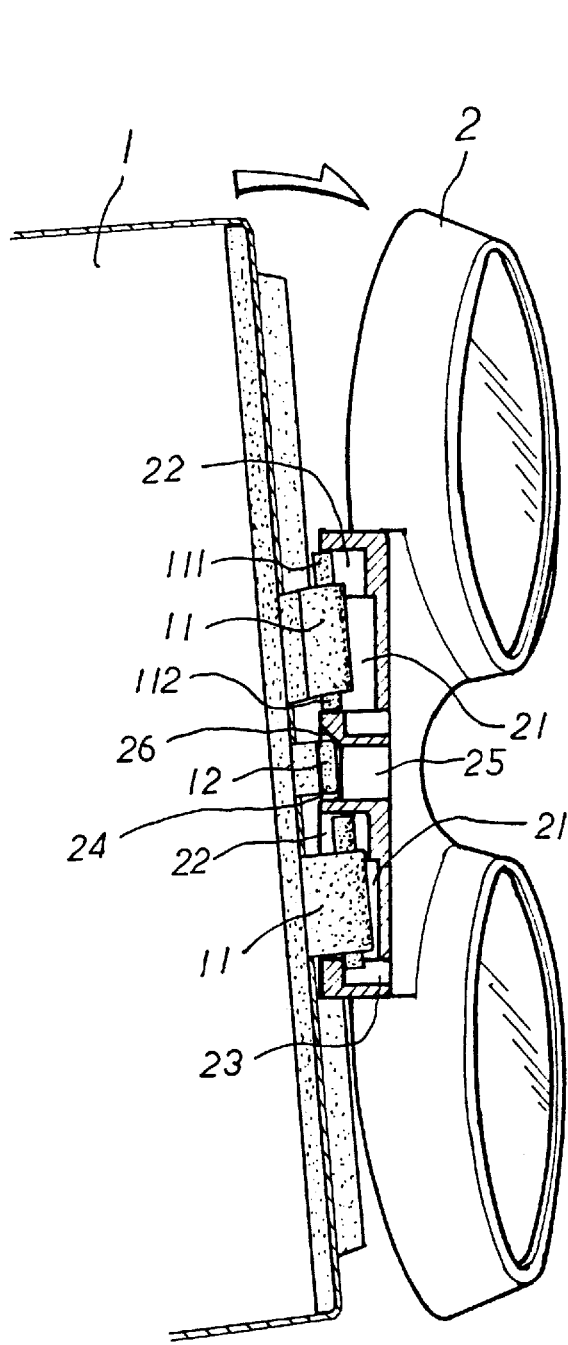
FIG. 6 illustrates the assembly of the safety goggles according to the present invention.
Figure 7:
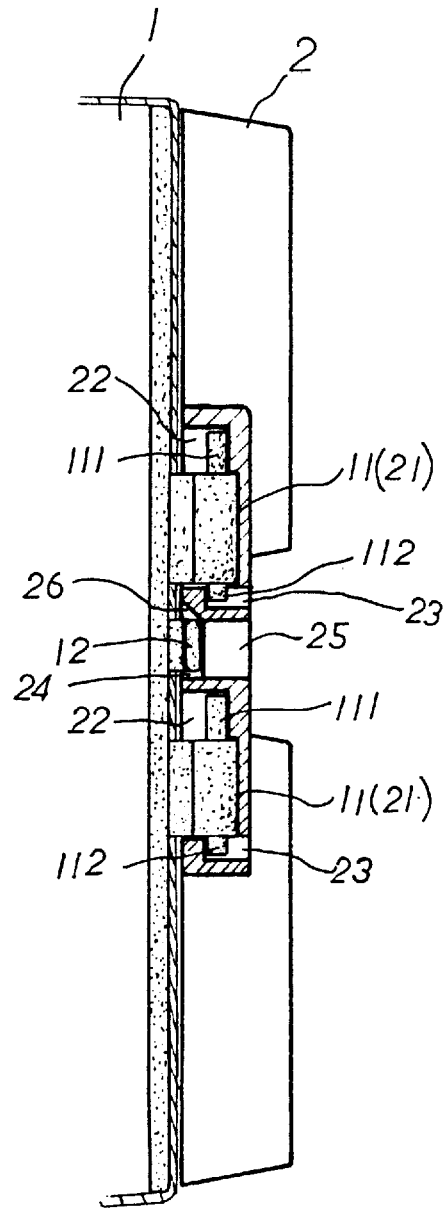
FIG. 7 is a sectional top view of the safety goggles according to the present invention.

The lens frame 2 is provided at the top with two cavities 21 aligned with the two raised seats 11. Each of the cavities 21 is formed with a groove 22 and an opening 23 configured to receive the long pin 111 and the short pin 112 respectively. A recess 24 is formed between the two cavities 21 and aligned with the tongue 12. The recess 24 has an inclined surface 25 at an outer side thereof and a chamfer 26 at an inner side thereof located close to the opening 23 of the raised seat 21 at the upper position (with respect to FIGS. 6 and 7).

When in assembly, the short pins 112 of the two raised seats 11 of the primary frame 1 are first forced into the openings 23 of the cavities 21 of the lens frame 2, and then the long pins 111 are pushed into the grooves 22. In the meantime, the tongue 12 is forced along the chamfer 26 into the recess 24 thereby firmly engaging the lens frame 2 with the primary frame 1 (see FIG. 7).

As the tongue 12, the long pins 111 and the short pins 112 are engaged with the recess 24, the grooves 21 and the openings 23, the lens frame 2 will not be detached from the primary frame 1 accidentally. In addition, the long pin 111 may have the same length as the short pin 111. Accordingly, the safety goggles according to the present invention are suitable for protecting one's eyes in gas welding or cutting operation. Furthermore, the lens frame is directly force-fitted in the primary frame without using any separate pivot means thereby simplifying the assembly and lowering the cost.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. Safety goggles comprising:

a primary frame having a top provided with two raised seats and an upwardly extending tongue between said two raised seats, each of said seats having a first pin extending outwardly longitudinally from an end thereof and a second pin extending outwardly longitudinally from another end thereof;

a lens frame having a top provided with two cavities aligned with said two raised seats, each of said cavities being formed with a groove and an opening configured to receive said first pin and said second pin respectively, a recess being formed between said two cavities and aligned with said tongue, said recess having an inclined surface at an outer side thereof and a chamfer at an inner side thereof, said chamfer being located close to said opening;

whereby when in assembly, said second pins are first forced into said openings of said lens frame, and then said first pins are pushed into said grooves thereby forcing said tongue into said recess and therefore firmly engaging said lens frame with said primary frame.

2. The safety goggles as claimed in claim 1, wherein said recess has an inner side formed with a chamfer close to said opening.

3. The safety goggles as claimed in claim 1, wherein said first and second pins are of different length.

* * * * *